United States Patent
Pignol et al.

(10) Patent No.: US 8,642,591 B2
(45) Date of Patent: Feb. 4, 2014

(54) COMPOSITION CONTAINING AMIDINE DERIVATIVES OR CARBOXAMIDE DERIVATIVES AND STEROIDS, AS A MEDICAMENT

(75) Inventors: Bernadette Pignol, Paris (FR); Serge Auvin, Palaiseau (FR); Dennis Bigg, Gif sur Yvette (FR); Pierre-Etienne Chabrier de Lassauniere, Paris (FR)

(73) Assignee: Ipsen Pharma S.A.S., Boulogne-Billancourt (FR)

( * ) Notice: Subject to any disclaimer, the term of this patent is extended or adjusted under 35 U.S.C. 154(b) by 356 days.

(21) Appl. No.: 12/282,131

(22) PCT Filed: Mar. 6, 2007

(86) PCT No.: PCT/FR2007/000390
§ 371 (c)(1),
(2), (4) Date: Feb. 5, 2009

(87) PCT Pub. No.: WO2007/101937
PCT Pub. Date: Sep. 13, 2007

(65) Prior Publication Data
US 2009/0149430 A1  Jun. 11, 2009

(30) Foreign Application Priority Data

Mar. 7, 2006  (FR) ..................................... 06 02000

(51) Int. Cl.
*A61K 31/54* (2006.01)
*A61K 31/56* (2006.01)
*A01N 45/00* (2006.01)

(52) U.S. Cl.
USPC ...................................... 514/225.2; 514/171

(58) Field of Classification Search
USPC ............................................. 514/225.2, 171
See application file for complete search history.

(56) References Cited

U.S. PATENT DOCUMENTS

| | | | |
|---|---|---|---|
| 4,244,942 A * | 1/1981 | Kamishita et al. | 514/179 |
| 6,747,024 B1 * | 6/2004 | Auvin et al. | 514/224.8 |
| 7,659,266 B2 * | 2/2010 | Auvin et al. | 514/225.2 |
| 7,696,197 B2 * | 4/2010 | Pignol et al. | 514/224.8 |

FOREIGN PATENT DOCUMENTS

| | | | | |
|---|---|---|---|---|
| EP | 1 618 881 A1 | 1/2006 | | |
| FR | WO2005/092345 | * 10/2005 | ......... | A61K 31/5415 |
| WO | WO 01/32654 | 5/2001 | | |
| WO | WO 2004/078908 A2 | 9/2004 | | |
| WO | WO 2005/056551 A2 | 6/2005 | | |

OTHER PUBLICATIONS

Cyrille Lescop, et al, Novel Cell-penetrating a-keto-amide Calpain Inhibitors as Potential Treatment for Muscular Dystrophy, 15 Bioorg. Med. Chem. Let. 5176 (2005).*
George Patani & Edmond LaVoie, Bioisosterism: A Rational Approach in Drug Design, 96 Chem. Rev. 3147, 3155 (1996).*
Susanne Kunz, et al, The Calpain Inhibitor MDL 28170 Prevents Inflammation-Induced Neurofilament Light Chain Breakdown in the Spinal Cord and Reduces Thermal Hyperalgesia, 110 Pain 409 (2004).*
International Search Report (Form PCT/ISA/210) in PCT/FR2007/000390.
Auvin, et al., "Novel dual inhibitors of calpain and lipid peroxidation," Bioorganic & Medicinal Chemistry Letters, vol. 14, No. 14, pp. 3825-3828 (2004).
Walter, et al., "Novel approaches to treat muscular dystrophies," Expert Opinion on Investigational Drugs, Vo. 10, No. 4, pp. 695-707 (2001).
Brauniger et al., "Zur Kernacylierung von 3-Methylphenothiazin," Pharmazie (1966), 21(11):645-649.
Gould, "Salt Selection for Basic Drugs," Int. J. Pharm. (1986) 33:201-217.
Katritzky et al., "Specific Synthesis of 1-Substituted Phenothiazines Using Carbon Dioxide Protection of the NH Group During Lithiation," Synthesis (1988) 3:215-217.
Manchand et al, "Synthesis of Carprofen, a Carbazole-Based Non-Steroidal Anti-Inflammatory Agent," Heterocycles (1994), 39(2):833-845.
Messer et al., "Cyclisation de Certains Azido-2 Diphenylsulfures en Phenothiazines; Transposition d'un type nouveau," Bull. Soc. Chim., 1968 7:2832-2842.
Narasimhan, "A New Efficient Synthesis of Pyridocarbazoles," J. Chem. Soc. Chem. Comm. (1985) 2:86-87.
Patel "Synthesis of Formylcarbazole Derivatives and Acetylcarbazole," J. Indian Chem. Soc. (1985), 62(7):534-536.
Schneider et al., "Darstellung von 7-Fluorphenothiazinen aus 2-Nitrodiarylsulfiden," Pharmazie, (1984) 39(1):22-23.
T.W. Green and P.G.M. Wuts, Protective Groups in Organic Synthesis, Second Edition, Table of Contents (Wiley-Interscience, 1991).
Vanderhaeghe, "Phenoxazines. I. Ring-Substituted Derivatives," J. Org. Chem. (1960), 25:747-753.
Yu et al., "Phenothiazines as Lipid Peroxidation Inhibitors and Cytoprotective Agents," J. Med. Chem. (1992), 35(4):716-724.

* cited by examiner

*Primary Examiner* — Sean Basquill
(74) *Attorney, Agent, or Firm* — Hunton & Williams LLP

(57) ABSTRACT

The present invention relates to a composition containing at least one amidine derivative or carboxamide derivative of general formula (I) or (A) in combination with at least one compound chosen from steroids, corticoids or corticosteroids, wherein said composition is suitable for the preparation of a medicament.

6 Claims, No Drawings

COMPOSITION CONTAINING AMIDINE DERIVATIVES OR CARBOXAMIDE DERIVATIVES AND STEROIDS, AS A MEDICAMENT

A subject of the present invention is a composition containing at least one amidine or carboxamide derivative in combination with at least one compound chosen from the steroids, corticoids or corticosteroids. The invention also relates to the pharmaceutical compositions containing this composition and their use for therapeutic purposes, in particular as calpain inhibitors and/or lipidic peroxidation inhibitors.

Given the potential role of the calpains and free radicals in physiopathology, the novel compositions according to the invention can produce effects which are beneficial or favourable in the treatment of pathologies where these enzymes (calpains) and reactive oxygen species (free radicals) are involved, and in particular for treating the diseases and disorders chosen from inflammatory or immunological diseases, cardiovascular diseases, cerebro-vascular diseases, disorders of the central or peripheral nervous system, cachexia, sarcopenia, hearing loss, osteoporosis, muscular dystrophies, cancerous or non-cancerous proliferative diseases, cataract, rejection reactions following organ transplantations, auto-immune diseases, viral diseases, nephrotoxicity or cancer.

In order to respond to industrial requirements, it has become necessary to find new calpain inhibiting and/or lipidic peroxidation inhibiting medicaments.

Thus the problem which the invention proposes to solve is to provide novel compositions capable of inhibiting the calpains and/or inhibiting lipidic peroxidation.

Unexpectedly, the inventors have demonstrated that the compositions containing at least one compound of general formula (I) or (A) described hereafter or their salts, in the racemic form, diastereoisomers or all combinations of these forms and at least one compound chosen from the steroids, corticoids or corticosteroids having an activity capable of treating diseases and disorders chosen from inflammatory or immunological diseases, cardiovascular diseases, cerebro-vascular diseases, disorders of the central or peripheral nervous system, cachexia, sarcopenia, hearing loss, osteoporosis, muscular dystrophies, cancerous or non-cancerous proliferative diseases, cataract, rejection reactions following organ transplantations, auto-immune diseases, viral diseases, nephrotoxicity or cancer.

Advantageously the composition according to the invention can produce effects which are beneficial or favourable in the treatment of the following pathologies:
- inflammatory and immunological diseases such as for example rheumatoid arthritis, pancreatitis, multiple sclerosis, inflammation of the gastro-intestinal tract (for example ulcerative or non-ulcerative colitis, Crohn's disease),
- cardiovascular and/or cerebro-vascular diseases comprising, for example, arterial hypertension, septic shock, cardiac or cerebral infarction of ischemic or haemorrhagic origin, ischemias as well as disorders linked to platelet aggregation.
- disorders of the central or peripheral nervous system such as, for example, neurodegenerative diseases where there can, in particular, be mentioned trauma to the brain or spinal cord, sub-arachnoid hemorrhages, epilepsy, ageing, senile dementia, including Alzheimer's disease, Huntington's chorea, Parkinson's disease, peripheral neuropathies,
- cachexia,
- sarcopenia,
- hearing loss, in particular hearing loss caused by presbycusis, acoustic trauma, or by administration of a medicament such as antibiotics, such as, for example, gentamycin, anti-cancer medicaments such as, for example, cisplatin, non-steroidal anti-inflammatories such as, for example, salicylic acid or ibuprofen derivatives, diuretics such as, for example, furosemide, anti-ulcer medicaments such as, for example, cimetidine or omeprazole, anticonvulsive agents such as, for example, carbamazepine or valproic acid,
- osteoporosis,
- muscular dystrophies, such as, for example, in particular Duchenne's muscular dystrophy, Becker's muscular dystrophy, myotonic muscular dystrophy or Steiner's disease, congenital muscular dystrophy, limb-girdle muscular dystrophy and facioscapulohumeral muscular dystrophy,
- non-cancerous proliferative diseases such as, for example, atherosclerosis or recurrence of stenosis,
- cataract,
- organ transplantations,
- auto-immune or viral diseases such as, for example, lupus, AIDS, parasitic or viral infections, diabetes and its complications,
- nephrotoxicity induced by antibiotics such as inter alia the aminoglycosides such as for example gentamycin,
- cancer and cancerous proliferative diseases.
- all the pathologies characterized by activation of the calpains.
- all the pathologies characterized by an increased production of free radicals.

Another advantage of the present invention is that the combination according to the invention has a synergy compared with the compounds used separately.

Still more advantageously, the composition according to the invention can make it possible to block or slow down the degeneration of the cells in particular of the muscle cells.

The invention also has the advantage of being able to have a protective effect on the cells vis-à-vis cell death.

In the case of the treatment of muscular dystrophy, the invention has the advantage of proposing an alternative treatment to the usual treatments, and in particular of making it possible to reduce the doses of corticoids currently used either by increasing the effectiveness of the treatment or without losing the effectiveness of this treatment. This another advantage which makes it possible to reduce or delay side-effects due to corticoids.

The composition according to the invention also has the advantage of possibly being useful for treating hearing loss.

An advantage of the invention is that it can be implemented in all industries, in particular the pharmaceutical, veterinary, cosmetic, and food industries, as well as in agricultural fields.

The compositions according to the invention or their salts have increased solubility in biological media, in particular in aqueous media.

Other advantages and characteristics of the invention will become clearly apparent on reading the following description and examples which are given purely by way of illustration and are not limitative.

A subject of the present invention is firstly a composition containing at least one compound chosen from the steroids, corticoids or corticosteroids or their salts and containing at least one compound chosen from either a) the compounds of general formula (I) or their salts

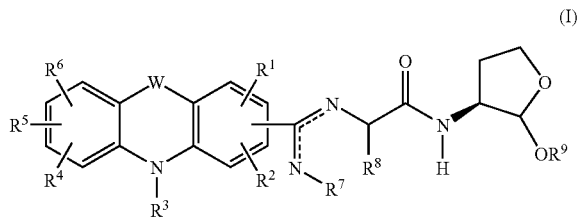

or b) the compounds of general formula (A) or their salts

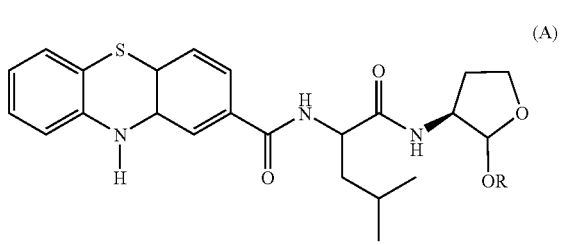

in racemic form, diastereoisomers, or all combinations of these forms
in which:

$R^1$, $R^2$, $R^4$, $R^5$ and $R^6$ represent, independently, a hydrogen atom, a halogen atom, the OH group, an alkyl, alkoxy, cyano, nitro, amino, alkylamino radical or carboxylic acid;

$R^3$ represents a hydrogen atom, an alkyl radical or a —$COR^{10}$ group;

$R^{10}$ represents a hydrogen atom or an alkyl, alkoxy, aryl radical, or a heterocyclic radical;

W represents an oxygen atom or a sulphur atom or —W— represents a bond;

$R^7$ represents a hydrogen atom or an alkyl radical;

$R^8$ represents a hydrogen atom, a haloalkyl or alkenyl radical, a cycloalkyl radical, a linear or branched alkyl radical, substituted or not, which when it is substituted carries a chemical function such as carboxylic acid, amino, alcohol, guanidine, amidine, thiol, thioether, thioester, alkoxy, heterocyclic or carboxamide;

$R^9$ represents a hydrogen atom, an alkyl, aryl, arylalkyl, bisarylalkyl radical, a heterocyclic radical, a heterocyclic alkyl radical or a —$COR^{10}$ group;

it being understood that:

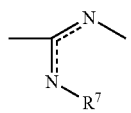

means

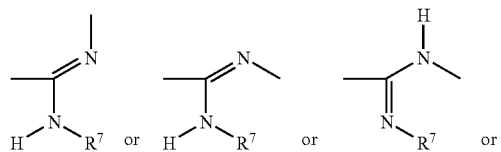

or

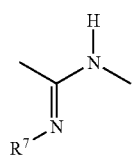

in racemic form, diastereoisomers or all combinations of these forms
in which R represents the hydrogen atom or —C(O)R' in which R' represents an alkyl radical.

The composition according to the invention comprises as first constituent at least one compound of general formula (I) described above or at least one compound of general formula (A) described above or their salts.

Preferably the compound of general formula (I) described above has an $R^1$ radical which is a hydrogen atom.

Preferably the compound of general formula (I) described above has an $R^2$ radical which is a hydrogen atom.

Preferably the compound of general formula (I) described above has an $R^3$ radical which is a hydrogen atom.

Preferably the compound of general formula (I) described above has an $R^4$ radical which is a hydrogen atom.

Preferably the compound of general formula (I) described above has an $R^5$ radical which is a hydrogen atom.

Preferably the compound of general formula (I) described above has an $R^6$ radical which is a hydrogen atom.

Preferably the compound of general formula (I) described above has an $R^7$ radical which is a hydrogen atom.

Preferably the compound of general formula (I) described above has an $R^8$ radical which is an isobutyl radical.

Preferably the atom W of the compound of general formula (I) described above is a sulphur atom.

Preferably the compound of general formula (I) described above has an $R^9$ radical which is a hydrogen atom.

Preferably the compound of general formula (I) described above has an $R^9$ radical which is an acetyl radical.

Preferably the compound of general formula (I) described above has an $R^9$ radical which is a methyl radical.

Preferably the compound of general formula (I) described above has an $R^9$ which is a benzyl radical.

Preferably the compound of general formula (I) described above has an $R^9$ radical which is a naphthylmethyl radical.

Preferably the compound of general formula (A) described above has an R radical which is a —C(O)—$CH_3$ radical.

By alkyl, unless defined otherwise, is meant a linear or branched alkyl radical containing 1 to 12 carbon atoms, and preferably 1 to 6 carbon atoms, even more preferentially 1 to 4 carbon atoms.

By linear or branched alkyl having 1 to 6 carbon atoms, is meant in particular the methyl, ethyl, propyl, isopropyl, butyl, isobutyl, sec-butyl and tert-butyl, pentyl, neopentyl, isopentyl, hexyl, isohexyl radicals.

By haloalkyl, is meant an alkyl radical at least one of the hydrogen atoms of which is substituted by a halogen atom. By haloalkyl, is meant for example the —$CF_3$, —$CHF_2$ or —$CH_2Cl$ radical.

By alkenyl, unless defined otherwise, is meant a linear or branched alkenyl radical having at least 1 unsaturation and containing 2 to 12 carbon atoms, and preferably 2 to 6 carbon atoms.

By alkoxy, unless defined otherwise, is meant an R—O— radical the carbon-containing chain R of which is linear or branched and has 1 to 6 carbon atoms.

By cycloalkyl, unless defined otherwise, is meant a saturated carbocyclic radical containing 3 to 7 carbon atoms. By cycloalkyl containing 3 to 7 carbon atoms, is meant in particular a cyclohexyl radical.

By aryl, unless defined otherwise, is meant an aromatic carbocyclic radical, preferably having 1 to 3 fused rings. By aryl, is meant in particular the phenyl, naphthyl and phenantryl radicals, preferably the phenyl and naphthyl radicals and more preferentially the phenyl radical.

By arylalkyl radicals is meant arylalkyl radicals of which their component alkyl and aryl radicals respectively have the meanings given above, it being understood that the aryl radical is attached to the (I) molecule via an alkyl radical.

By bisarylalkyl is meant in the sense of the present invention an aromatic carbocyclic radical comprising at least 2 rings, at least one of which is aromatic, and comprising at most 14 carbon atoms, preferably at most 10 carbon atoms, it being understood that the bisarylalkyl radical is attached to the (I) molecule via an alkyl radical.

By heterocyclic, is meant in the sense of the present invention a cyclic radical which is aromatic or not comprising 1 to 14 atoms, these atoms being chosen from carbon, nitrogen, oxygen or sulphur, or one of their combinations. It is understood that the heterocyclic radical can be partially unsaturated. By heterocyclic, is meant for example a heteroaryl radical or a heterocycloakyl radical.

By heterocyclic alkyl, is meant in the sense of the present invention a heterocyclic alkyl radical of which the heterocyclic and alkyl radicals which comprise them have the meanings indicated above and the heterocyclic radical of which is attached to the (I) molecule via a an alkyl radical.

By halogen atom is meant an atom chosen from fluorine, chlorine, bromine or iodine atoms.

By amino, is meant in the sense of the present invention an —NH$_2$ radical.

By alkylamino, is meant in the sense of the present invention an —NRH or —N(R")$_2$ radical with R being an alkyl radical as defined previously.

The following examples indicate the protective groups which can protect functions carried by the R$^8$ radical:

methyl, ethyl, tert-butyl or benzyl esters can protect acid functions;

benzyl or fluorenylmethyl tert-butyl carbamates can protect the amine functions;

acetamides can protect amine functions; and tetrahydropyrane or silyl, benzyl, tert-butyl ethers can protect alcohol functions; and acetyls can protect alcohol functions; and methyl thioethers or methyl thioesters can protect thiol functions.

In particular, the invention relates to a composition comprising at least one compound chosen from the following compounds or their salts:

N$^2$-[imino(10H-phenothiazin-2-yl)methyl]-N$^1$-[(3S)-2-methoxytetrahydrofuran-3-yl]-L-leucinamide;
N$^1$-[(3S)-2-(benzyloxy)tetrahydrofuran-3-yl]-N$^2$-[imino(10H-phenothiazin-2-yl)methyl]-L-leucinamide;
N$^2$-[imino(10H-phenothiazin-2-yl)methyl]-N$^1$-[(3S)-2-(2-naphthylmethoxy)tetrahydrofuran-3-yl]-L-leucinamide;
(3S)-3-({N-[imino(10H-phenothiazin-2-yl)methyl]-L-leucyl}amino)tetrahydrofuran-2-yl acetate;
N$^1$-[(3S)-2-hydroxytetrahydrofuran-3-yl]-N$^2$-[imino(10H-phenothiazin-2-yl)methyl]-L-leucinamide.
N-[(1S)-1-({[(2S)-2-hydroxytetrahydrofuran-3-yl]amino}carbonyl)-3-methylbutyl]-10H-phenothiazine-2-carboxamide;
N-[(1S)-1-({[(2R)-2-hydroxytetrahydrofuran-3-yl]amino}carbonyl)-3-methylbutyl]-10H-phenothiazine-2-carboxamide;
N-[(1R)-1-({[(2S)-2-hydroxytetrahydrofuran-3-yl]amino}carbonyl)-3-methylbutyl]-10H-phenothiazine-2-carboxamide;
N-[(1R)-1-({[(2R)-2-hydroxytetrahydrofuran-3-yl]amino}carbonyl)-3-methylbutyl]-10H-phenothiazine-2-carboxamide;
(2R,3S)-3-{[N-(10H-phenothiazin-2-ylcarbonyl)-L-leucyl]amino}tetrahydrofuran-2-yl acetate;
(2S,3S)-3-{[N-(10H-phenothiazin-2-ylcarbonyl)-L-leucyl]amino}tetrahydrofuran-2-yl acetate;
(2R,3S)-3-{[N-(10H-phenothiazin-2-ylcarbonyl)-D-leucyl]amino}tetrahydrofuran-2-yl acetate;
(2S,3S)-3-{[N-(10H-phenothiazin-2-ylcarbonyl)-D-leucyl]amino}tetrahydrofuran-2-yl acetate;
(3S)-3-{[N-(10H-phenothiazin-2-ylcarbonyl)-L-leucyl]amino}tetrahydrofuran-2-yl acetate.

The terminology used for the nomenclature of the compounds above is the English IUPAC terminology.

The composition according to the invention comprises as second constituent at least one compound chosen from the steroids, corticoids or corticosteroids or their salts.

Among the steroids which are suitable according to the invention, there can be mentioned dexamethasone the chemical formula of which is 9 alpha-fluoro-11 beta, 17 alpha, 21-trihydroxy-16 alpha-methylpregna-1,4-diene-3,20-dione 21-isonicotinate, there can also be mentioned oxandrolone the chemical formula of which is hydroxy-17 beta methyl-17 oxo-3 oxa-2 5 alpha-androstane.

Among the corticoids which are suitable according to the invention, there can be mentioned cortisone or one of its derivatives.

Among the corticosteroids which are suitable according to the invention, there can be mentioned:

prednisone: 11β,17α,21-trihydroxypregna-1,4-diene-3,20-dione Corticosteroid;

prednisolone: 17α,21-dihydroxypregna-1,4-diene-3,11,20-trione Corticosteroid;

α-methylprednisolone;

deflazacort which is an oxazolone derivative of prednisone.

A subject of the present invention is also a compound as defined above for use as a therapeutically active substance.

Even more particularly, the compounds according to the invention and as defined above can be used as a therapeutically active substance for treating diseases and disorders chosen from inflammatory or immunological diseases, cardiovascular diseases, cerebro-vascular diseases, disorders of the central or peripheral nervous system, cachexia, sarcopenia, hearing loss, osteoporosis, muscular dystrophies, proliferative diseases whether cancerous or not, cataract, rejection reactions following organ transplantations, auto-immune diseases, viral diseases or cancer.

Preferably, a subject of the invention is a composition according to the invention and as defined above, for its use as a therapeutically active substance for the treatment of hearing loss.

Preferably a subject of the invention is a composition according to the invention, for its use as a therapeutically active substance for treating muscular dystrophies, in particular Duchenne's muscular dystrophy, Becker's muscular dystrophy, myotonic muscular dystrophy or Steiner's disease, congenital muscular dystrophy, limb girdle muscular dystrophy and facioscapulohumeral muscular dystrophy.

A subject of the present invention is also a medicament comprising at least one composition as defined previously, or one of its salts. Preferably these are pharmaceutically acceptable salts of such compounds.

As a medicament, the composition as defined previously or its pharmaceutically acceptable salts.

The invention also relates to pharmaceutical compositions containing at least one composition as defined previously, or at least one pharmaceutically acceptable salt of this compound. Preferably the pharmaceutical compound comprises at least one pharmaceutically acceptable excipient. Preferably, the compound according to the invention and as defined previously, or its salt, is contained in the pharmaceutically active composition as active ingredient.

By pharmaceutically acceptable salt, is meant in particular the addition salts of inorganic acids such as, for example, hydrochloride, hydrobromide, hydroiodide, sulphate, phosphate, diphosphate or nitrate or organic acids such as, for example, acetate, maleate, fumarate, tartrate, succinate, citrate, lactate, methanesulphonate, p-toluenesulphonate, benzenesulphonate, pamoate or stearate. For other examples of pharmaceutically acceptable salts, reference can be made to "Salt selection for basic drugs", *Int. J. Pharm.* (1986), 33, 201-217.

The composition according to the invention or its salt used according to the invention can be in the form of a solid, for example powders, granules, tablets, gelatin capsules, liposomes or suppositories. Appropriate solid supports can be, for example, calcium phosphate, magnesium stearate, talc, sugars, lactose, dextrin, starch, gelatin, cellulose, methyl cellulose, sodium carboxymethyl cellulose, polyvinylpyrrolidine or wax.

The composition according to the invention or its salt used according to the invention can be in the semi-solid form, for example in the form of a gel, a foam or a pomade.

The composition according to the invention or its salt can also be presented in liquid form, for example, solutions, emulsions in the broad sense, suspensions, sprays or syrups. Appropriate liquid supports can be for example water, organic solvents such as glycerol or glycols, as well as their mixtures, in varying proportions, in water.

The invention moreover relates to the use of a composition according to the invention and as defined previously, or of a pharmaceutically acceptable salt of such a composition, for preparing a medicament intended to treat the diseases and disorders chosen from inflammatory or immunological diseases, cardiovascular diseases, cerebro-vascular diseases, disorders of the central or peripheral nervous system, cachexia, sarcopenia, hearing loss, osteoporosis, muscular dystrophies, cancerous or non-cancerous proliferative diseases, cataract, rejection reactions following organ transplantations, the auto-immune diseases, viral diseases, or cancer.

The administration of a composition according to the invention or its salt can be carried out by topical, oral, parenteral route, by intravenous, intramuscular, sub-cutaneous injection, etc.

The dose of the composition according to the present invention, to be provided for the treatment of the diseases or disorders mentioned above, varies according to the administration method, the age and body weight of the patient to be treated as well as the state of the latter, and will be decided definitively by the attending doctor or vet. Such a quantity determined by the attending doctor or vet is known here as the "therapeutically active quantity".

According to an embodiment of the compositions according to the invention, the ratio of the constituents [first constituent/second constituent] can be comprised between 1/99 and 99/1, advantageously between 5/95 and 95/5, or between 10/90 and 90/10.

According to a variant of the composition according to the invention, the ratio of the constituents is 50/50.

According to another variant of the composition according to the invention, the ratio of the constituents is 80/20.

According to another variant of the composition according to the invention, the ratio of the constituents is 20/80.

According to another variant of the composition according to the invention, the ratio of the constituents [first constituent/second constituent] is comprised between 30/70 and 1/99.

A subject of the invention is also the use of the composition according to the invention or its salt in the pharmaceutical, veterinary, chemical, cosmetic, foodstuffs industries, as well as in agricultural fields.

Preparation of the Compounds of General Formula (I)

The compounds of general formula (I) according to the invention can be prepared according to the synthesis route shown in Diagram 1 below. The compounds of general formula (I) in which $R^9$ represents an alkyl, aryl, arylalkyl, bisarylalkyl radical, a heterocyclic radical, a heterocyclic alkyl radical or a —$COR^{10}$ group with $R^{10}$ representing a hydrogen atom or an alkyl, alkoxy, aryl radical, or a heterocyclic radical are known as the compounds of general formula $(I)_1$. The compounds of general formula (I) in which $R^9$ represents a hydrogen atom are known as the compounds of general formula $(I)_2$ in the remainder of the description. In Diagram 1 below, as well as Diagram 2, the meaning of W, $R^1$, $R^2$, $R^3$, $R^4$, $R^5$, $R^6$, $R^7$, $R^8$, $R^9$, $R^{10}$ and $R^{11}$ in the compounds of general formulae (II), (III), $(I)_1$ and $(I)_2$, is as previously stated in the description:

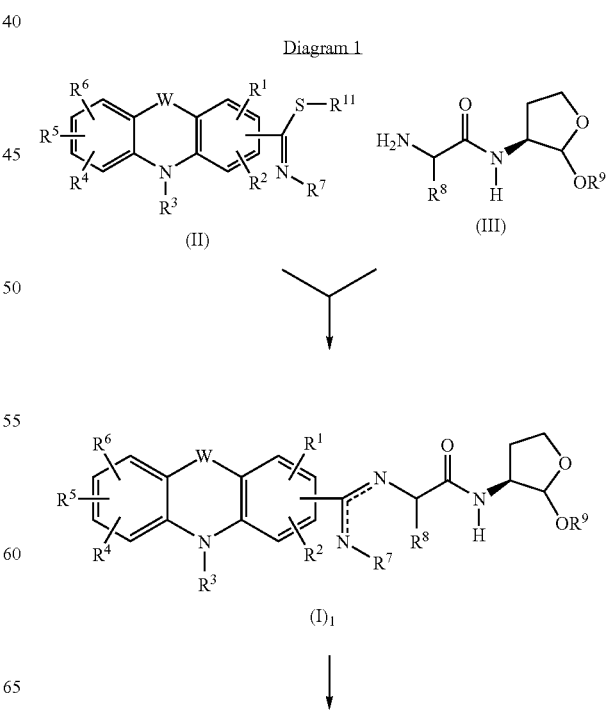

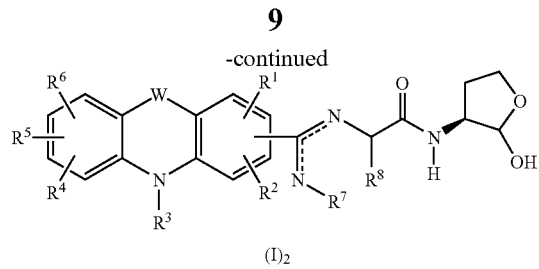

(I)₂

The compounds of general formulae (I)₁ and (I)₂ are obtained according to Diagram 1 by condensation of the thioimidate derivatives of general formula (II) with the amino-lactols of general formula (III), preferably by heating between 25 and 60° C., preferentially in a polar solvent, such as for example isopropanol, DMF or even THF, for a period of 4 to 20 hours. The hemiacetal function of the compounds of general formula (I)₁ can then be deprotected in order to produce the compound of general formula (I)₂, for example in an acid medium, using an inorganic acid such as HCl or HBr or an organic acid, such as for example benzene sulphonic acid, in solution in an organic solvent such as for example acetone, THF, dioxane, acetonitrile or ethanol. The reaction generally is carried out at about 20° C. and for a time varying from 4 to 20 hours according to the nature of $R^9$.

Preparation of the Intermediates of General Formula (II):

The non-commercial thioimidates of general formula (II), in which W, $R^1$, $R^2$, $R^3$, $R^4$, $R^5$, $R^6$ and $R^7$ are as described above in the description, can be prepared according to the synthesis route detailed in Diagram 2.

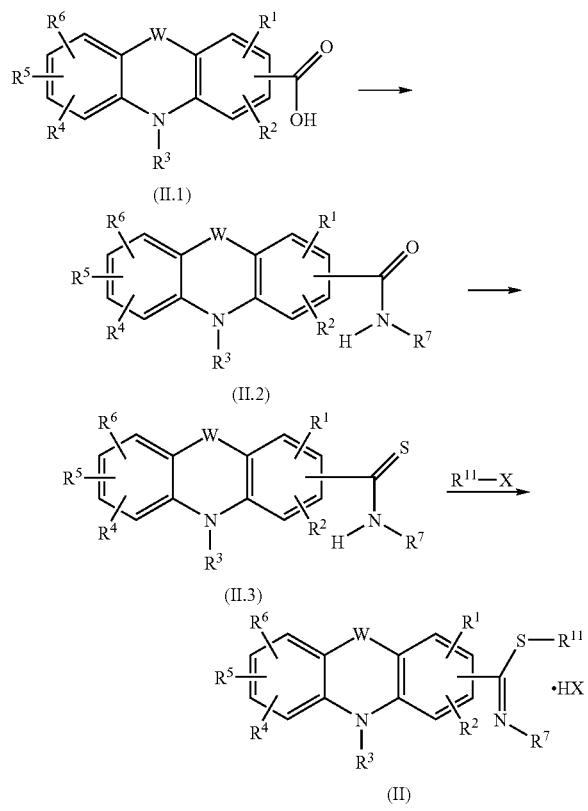

The thioimidates of general formula (II), derivatives of phenothiazine (W=S), phenoxazine (W=O) or carbazole (—W— is a bond) can be obtained in 3 stages starting from the corresponding carboxylic acids of general formula (II.1). These carboxylic acids are accessible from methods described in the literature such as, for example, *Pharmazie* 1984, 39(1), 22-3; *Bull. Soc. Chim.* 1968, (7), 2832-42, *Pharmazie* 1966, 21(11), 645-9, *Synthesis* 1988, (3), 215-17, *J. Med. Chem.* 1992, 35(4), 716-24, *J. Org. Chem.* (1960), 25, 747-53, *Heterocycles* (1994), 39(2), 833-45; *J. Indian Chem. Soc.* (1985), 62(7), 534-6; *J. Chem. Soc. Chem. Comm.* (1985), (2), 86-7. The formation of the carboxamides of general formula (II.2) is carried out in the presence of a concentrated aqueous solution of ammonia ($R^7$=H) or an amine ($R^7$=alkyl), using a peptide coupling reagent, such as for example DCC or HBTU, in a solvent such as for example DMF. The thiocarboxamides of general formula (II.3) can be obtained by the action of Lawesson reagent in solution in 1,4-dioxane. The alkylation of the thiocarboxamides to generate the thioimidates of general formula (II) can be performed using $R^{11}$—X, X being a leaving group such as for example a halogen atom, a sulphate or triflate group. The reaction mixture is for example stirred in acetone for 15 hours. The thioimidates (II) are obtained in the form of salts, for example, hydroiodide if iodomethane ($R^{11}$—X) is used, and can optionally be desalified using a base such as, for example, sodium carbonate.

Preparation of the Intermediates of General Formula (III):

The amino-lactol derivatives of general formula (III), in which $R^8$ and $R^9$ are as described above, with Gp being a protective group preferably of the carbamate type, are accessible by using, for example, the preparation routes shown in Diagram 3 below.

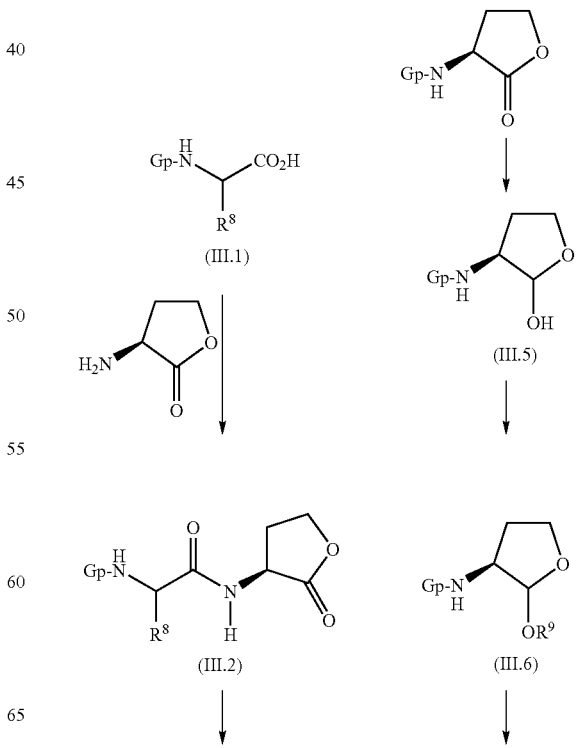

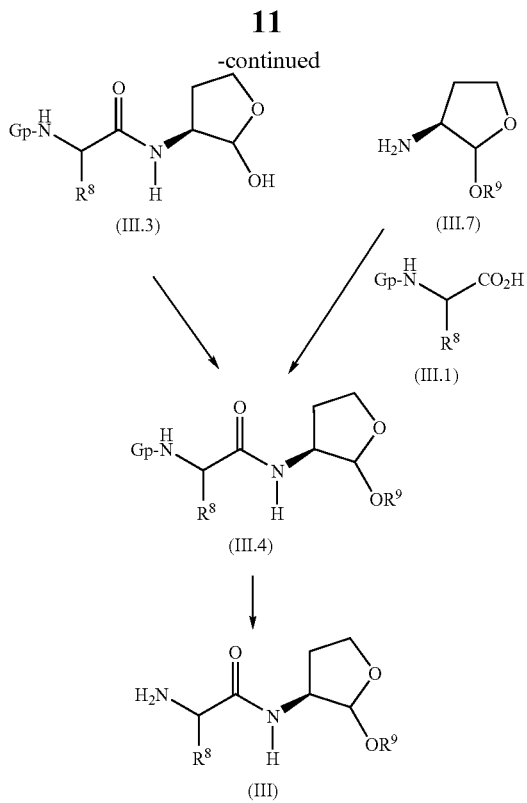

The amino-butyrolactone derivatives of general formula (III.2) can be obtained by condensation of the protected amino acids of general formula (III.1), in which $R^8$ is an amino acid radical as defined previously in general formula (I) and Gp is a protective group such as, for example, a benzyl, tert-butyl or fluorenylmethyl carbamate, with (S)-α-aminobutyrolactone under standard conditions for peptide synthesis in order to produce the carboxamide intermediates of general formula (III.2). The lactone (III.2) is then reduced to lactol using a reducing agent such as, for example, diisobutylaluminium hydride (DIBAL), in an inert solvent such as, for example, THF or $CH_2Cl_2$, at a temperature preferably below −50° C., for example, approximately −78° C. The hemiacetal function of the lactol derivatives of general formula (III.3) is then protected either in an alcohol medium, for example in methanol or benzyl alcohol, using a strong acid such as, for example, trifluoroacetic or camphorsulphonic acid, or in the presence of a carboxylic acid anhydride, for example acetic anhydride, in the presence of 4-dimethylaminopyridine in an inert solvent, such as dichloromethane, in order to produce the acetals of general formula (III.4).

Alternatively, the amino-lactols of general formula (III), can be prepared in 5 stages starting from commercial protected (S)-α-aminobutyrolactones. The successive stages of reduction of the lactone and protection of the hemiacetal in order to produce the intermediates (III.5) and (III.6) are identical to those described for generation of the intermediates (III.3) and (III.4). The preparation of the intermediates (III.7) is carried out preferably by hydrogenolysis, in the presence of Pd/C, of the benzyloxycarbonyl group principally used in this strategy. The intermediates of general formula (III.4) can then be obtained by peptide condensation under the conditions described previously for (III.2), between the intermediates (III.7) and the amino acids of general formula (III.1). The amine function of the intermediates of general formula (III.4) is then deprotected according to the methods described in the literature (T. W. Greene and P. G. M. Wuts, Protective Groups in Organic Synthesis, Second edition (Wiley-Interscience, 1991)).

Unless defined otherwise, all the technical and scientific terms used here have the same meaning as that usually understood by an ordinary specialist in the field to which this invention belongs. Similarly, all the publications, patent applications, all the patents and all other references mentioned here are incorporated by way of reference.

Preparation of the Compounds of General Formula (A)

The preparation of the compounds of general formula (A) is described in the Application WO 01/32654.

The following examples are given to illustrate the procedures above and should in no way be considered as limiting the scope of the invention.

EXAMPLES

The terminology used for the nomenclature of the examples below is the English IUPAC terminology.

In the following examples, the melting points were measured by means of a capillary using a device with the trade name Büchi, model B-545.

Example 1

$N^2$-[imino(10H-phenothiazin-$^2$-yl)methyl]-$N^1$-[(3S)-2-methoxytetrahydrofuran-3-yl]-L-leucinamide hydroiodide 1.1) $N^2$-[(benzyloxy)carbonyl]-$N^1$-[(3S)-2-oxotetrahydrofuran-3-yl]-L-leucinamide 3.51 g (13.25 mmol) of Cbz-L-Leucine, 2.41 g (1 eq.) of (S)-2-amino-4-butyrolactone hydrobromide, 1.97 g of HOBT (1.1 eq.) and 5.59 g (2.2 eq.) of 1-(3-dimethylaminopropyl)carbodiimide hydrochloride (EDC) are dissolved in 60 ml of anhydrous DMF, then 7.64 ml of (3.3 eq.) of N,N-diisopropylethylamine is added. The reaction mixture is stirred for 15 hours at 20° C. before being poured into 200 ml of a 1/1 mixture of ethyl acetate/water. After stirring and decantation, the organic solution is washed successively with 100 ml of a saturated solution of $NaHCO_3$, 50 ml of water, 100 ml of a 1M solution of citric acid and finally 100 ml of a solution of salt water. The organic phase is dried over sodium sulphate, filtered and concentrated to dryness under vacuum. The oil obtained is washed using isopentane and then crystallized from a dichloromethane/isopentane mixture. A white solid is obtained with a yield of 68%. Melting point: 130-131° C.

1.2) $N^2$-[(benzyloxy)carbonyl]-$N^1$-[(3S)-2-hydroxytetrahydrofuran-3-yl]-L-leucinamide 1.24 g (3.56 mmol) of intermediate 1.1 is dissolved under argon in a three-necked flask containing 60 ml of anhydrous dichloromethane. The mixture is cooled down to −60° C. before 10.7 ml of (3 eq.) of a 1M solution of DIBAL in dichloromethane is added dropwise. At the end of the addition, the cooling bath is removed and stirring is maintained for an additional 15 minutes. The reaction medium is then carefully poured into 100 ml of a 20% Rochelle salt solution. After 2 hours of vigorous stirring, 100 ml of dichloromethane is added and the whole is poured into a separating funnel. The organic phase is recovered and washed with 50 ml of water and 50 ml of salt water. After drying over sodium sulphate and filtration, the organic solution is concentrated to dryness under vacuum. The evaporation residue is purified using a silica column (eluent: heptane/AcOEt:1/1 to 2/8). A white solid is obtained with a yield of 72%. Melting point: 48-49° C.

1.3) $N^2$-[(benzyloxy)carbonyl]-$N^1$-[(3S)-2-methoxytetrahydrofuran-3-yl]-L-leucinamide An excess of trifluoroacetic acid (5 ml) is added dropwise at 20° C. to a solution of 0.82 g (2.34 mmol) of intermediate 1.2 in 50 ml of methanol. Stirring is maintained for 15 hours at 20° C. The reaction mixture is then partially concentrated under vacuum and redissolved in 50 ml of dichloromethane. The organic solution is washed successively with 50 ml of a saturated solution of $NaHCO_3$, 50 ml of water and 50 ml of salt water. After drying over sodium sulphate, filtration and concentration under vacuum, the evaporation residue is purified using a silica column (eluent: heptane/AcOEt:1/1 to 3/7). A white solid is obtained with a yield of 80%. Melting point: 112-113° C.

1.4) $N^1$-[(3S)-2-methoxytetrahydrofuran-3-yl]-L-leucinamide 2 g (5.5 mmol) of intermediate 1.3 and 600 mg of Pd/C at 10% are introduced into a stainless steel reactor containing 60 ml of methanol. The mixture is stirred under 2 atm. hydrogen pressure for 1 hour. After filtration of the catalyst, the methanol is evaporated off under vacuum. The oily residue obtained (1.20 g; 94%) is used as it is in the following stage.

1.5) 10H-phenothiazine-2-carbothioamide

A reaction mixture comprising 3.4 g (14 mmoles) of 10H-phenothiazine-2-carboxamide (*J. Org. Chem.* 1961, 26, 1138-1143) and 3.4 g (8.4 mmoles) of Lawesson reagent in solution in 40 ml of 1,4-dioxane to which 20 ml of pyridine has been added is heated at 110° C. for 1 h 30. The brown solution is then concentrated under vacuum and the residue is diluted in 200 ml of AcOEt and 100 ml of $H_2O$. After stirring and decantation, the organic phase is washed successively with 100 ml of a 1N aqueous solution of HCl and 100 ml of salt water. After drying over sodium sulphate, filtration and evaporation of the solvent under vacuum, an orange powder is obtained. This powder is washed with $Et_2O$, the filtrate is eliminated, and extracted with acetone. The acetone filtrate is then concentrated under vacuum and the evaporation residue is then purified using a silica column (eluent: Heptane/AcOEt:1/1 to 416). Orange powder. Melting point: 208-209° C.

1.6) Methyl 10H-phenothiazine-2-carbimidothioate hydroiodide 0.3 ml (1.2 eq.) of iodomethane is added at 23° C. to a solution of 1.05 g (4.1 mmoles) of intermediate 1.5 in 10 ml of acetone. The reaction mixture is stirred for 15 hours. The precipitate formed is filtered and rinsed successively with acetone and isopentane. A brown-violet solid is obtained with a yield of 85%. Melting point: 207-208° C.

1.7) $N^2$-[imino(10H-phenothiazin-$^2$-yl)methyl]-$N^1$-[(3S)-2-methoxytetrahydrofuran-3-yl]-L-leucinamide hydroiodide 1.18 g (1 eq.) of intermediate 1.6 is added to a solution of 0.68 g (2.95 mmoles) of intermediate 1.4 in 20 ml of isopropanol. The reaction mixture is stirred at 60° C. for 15 hours. The methanethiol released during the reaction is successively trapped using a solution of soda and a solution of potassium permanganate. The solid formed is isolated by filtration and rinsed with $Et_2O$ before being purified using a silica column (eluent: heptane/AcOEt:1/1 to 0/1). An orange solid is obtained with a yield of 70%. Melting point: 155-165° C.

Example 2

$N^1$-[(3S)-2-(benzyloxy)tetrahydrofuran-3-yl]-$N^2$-[imino(10H-phenothiazin-2-yl)methyl]-L-leucinamide hydroiodide

2.1) $N^2$-[(9H-fluoren-9-ylmethoxy)carbonyl]-$N^1$-[(3S)-2-otetrahydrofuran-3-yl]-L-leucinamide The experimental protocol used is the same as that described for the synthesis of intermediate 1.1, Fmoc-L-Leucine replacing Cbz-L-Leucine. 3.15 g of a white solid is obtained by crystallization from AcOEt with a yield of 72%. Melting point: 175-176° C.

2.2) $N^2$-[(9H-fluoren-9-ylmetoxy)carbonyl]-$N^1$-[(3S)-2-hydroxytetrahydrofuran-3-yl]-L-leucinamide The experimental protocol used is the same as that described for the synthesis of intermediate 1.2, with intermediate 2.1 replacing intermediate 1.1. After purification on a silica column (heptane/AcOEt: 1/1, 2.16 g white solid is obtained with a yield of 68%. Melting point: 155-156° C.

2.3) $N^1$-[(3S)-2-(benzyloxy)tetrahydrofuran-3-yl]-$N^2$-[(9H-fluoren-9-ylmethoxy)carbonyl]-L-leucinamide 0.41 ml (1.1 eq.) of benzyl alcohol and 0.11 g (0.13 eq.) of camphorsulphonic acid are added to a suspension of 1.57 g (3.58 mmoles) of intermediate 2.2 in 7 ml of dichloromethane. As the reaction proceeds, the reaction medium becomes homogeneous. After stirring for 24 hours, the mixture is diluted with 25 ml of water and 25 ml of dichloromethane, stirred and decanted. The organic solution is dried over sodium sulphate, filtered and concentrated to dryness. The residue is purified using a silica column (heptane/AcOEt: 1/0 to 1/1). After evaporation, 1.43 g white solid is obtained with a yield of 76%. Melting point: 116-117° C.

2.4) $N^1$-[(3S)-2-(benzyloxy)tetrahydrofuran-3-yl]-L-leucinamide 0.2 ml (5 eq.) of diethylamine is added dropwise to a solution of 0.2 g (0.38 mmol) of intermediate 2.3 in solution in 3.5 ml of dichloromethane. The reaction mixture is stirred at 23° C. for 5 h 30 before being concentrated to dryness under vacuum. The residue is partially redissolved with $Et_2O$ and stored at 4° C. for a few hours. The white precipitate formed is eliminated by filtration and the filtrate is concentrated to dryness. The evaporation residue is used as it is in the following stage.

2.5) $N^1$-[(3S)-2-(benzyloxy)tetrahydrofuran-3-yl]-$N^2$-[imino(10H-phenothiazin-2-yl)methyl]-L-leucinamide hydroiodide The experimental protocol used is the same as that described for the synthesis of intermediate 1.7, by reaction of intermediate 1.6 with intermediate 2.4 which is used in place of intermediate 1.4. The product of the reaction is purified using a silica column (heptane/AcOEt:1/1 to 0/1). After evaporation of the purest fractions, the residue is mixed in isopentane/AcOEt in order to produce a pale orange precipitate. 430 mg of the expected product is obtained with a yield of 53%. Melting point: 140-145° C.

Example 3

$N^2$-[imino(10H-phenothiazin-$^2$-yl)methyl]-$N^1$-[(3S)-2-(2-naphthylmethoxy)tetrahydrofuran-3-yl]-L-leucinamide hydroiodide 3.1) $N^2$-[(9H-fluoren-9-ylmethoxy)carbonyl]-$N^1$-[(3S)-2-(2-naphthylmethoxy)tetrahydrofuran-3-yl]-L-leucinamide The experimental protocol used is the same as that described for the synthesis of intermediate 2.3 starting from intermediate 2.2 and 2-hydroxymethylnaphthalene is used in place of the benzyl alcohol. After purification on a silica column (heptane/AcOEt:7/3) 1.38 g of a white solid is obtained with a yield of 66%. Melting point: 79-80° C.

3.2) $N^1$-[(3S)-2-(2-naphthylmethoxy)tetrahydrofuran-3-yl]-L-leucinamide

The experimental protocol used is the same as that described for the synthesis of intermediate 2.4, with intermediate 3.1 replacing intermediate 2.3. The product is obtained after elimination of the dibenzofulvene derivatives and is used as it is in the following stage.

3.3) $N^2$-[imino(10H-phenothiazin-$^2$-yl)methyl]-$N^1$-[(3S)-$^2$-($^2$-naphthyl methoxy)tetrahydrofuran-3-yl]-L-leucinamide hydroiodide The experimental protocol used is the same as that described for the synthesis of intermediate 1.7, starting from intermediate 1.6 and intermediate 3.2 used in place of intermediate 1.4. The product of the condensation reaction is purified using a silica column (heptane/AcOEt:1/1 to 0/1). After evaporation of the purest fractions, the residue is mixed in isopentane/AcOEt in order to produce an orange precipitate. 530 mg of the expected product is obtained with a yield of 64%. Melting point: 145-148° C.

Example 4

(3S)-3-({N-[imino(10H-phenothiazin-2-yl)methyl]-L-leucyl}amino)tetrahydrofuran-2-yl acetate hydroiodide 4.1) (3S)-3-({N-[(benzyloxy)carbonyl]-L-leucyl}amino)tetrahydrofuran-2-yl acetate 2 g (5.73 mmoles) of intermediate 1.2 and 0.14 g (0.2 eq.) of 4-dimethylaminopyridine are dissolved, under an argon atmosphere, in 13 ml of anhydrous dichloromethane. 5.4 ml (10 eq.) of acetic anhydride is added dropwise to this solution. After stirring for 5 hours at 23° C., the reaction mixture is diluted with 50 ml of dichloromethane and 50 ml of water. The organic phase is then washed successively with 50 ml of a saturated solution of $NaHCO_3$, 50 ml of water and finally salt water. The dichloromethane solution is dried over $Na_2SO_4$, filtered and concentrated to dryness under vacuum. The residue obtained is mixed with $Et_2O$, filtered and rinsed with isopentane. 1.14 g white solid is obtained with a yield of 50%. Melting point: 158-159° C.

4.2) (3S)-3-(L-leucylamino)tetrahydrofuran-2-yl acetate 1.14 g (2.89 mmoles) of intermediate 4.1 and 227 mg of Pd/C at 10% are introduced into a stainless steel reactor containing 30 ml of acetic acid. The mixture is stirred under 2 atm. of hydrogen pressure for 4 h 30. After filtration of the catalyst, the acetic acid is evaporated off under vacuum. The oily residue obtained is divided between 50 ml of dichloromethane and 50 ml of a saturated $NaHCO_3$ solution. Stirring and decantation are followed by washing the organic phase with water and salt water. After drying over $Na_2SO_4$, filtration and concentration to dryness, the colourless oil obtained crystallizes spontaneously in order to produce 0.45 g of a white solid with a yield of 60%. Melting point: 75-80° C.

4.3) (3S)-3-({N-[imino(10H-phenothiazin-2-yl)methyl]-L-leucyl}amino)tetrahydrofuran-2-yl acetate hydroiodide The experimental protocol used is the same as that described for the synthesis of intermediate 1.7, starting from intermediate 1.6 and intermediate 4.2 with the exception of the reaction solvent which in this case is THF, and the heating time which is limited to 4 hours. The reaction mixture is directly adsorbed on silica and deposited at the top of a chromatography column (heptane/AcOEt: 3/7 to 0/1) for purification. After collection and evaporation of the pure fractions, 0.27 g of an orange solid is obtained with a yield of 18%. Melting point: 130-131° C.

Example 5

$N^1$-[(3S)-2-hydroxytetrahydrofuran-3-yl]-$N^2$-[imino(10H-phenothiazin-2-yl)methyl]-L-leucinamide hydroiodide 12 mg (0.1 eq.) of benzenesulphonic acid is added to a solution of 0.42 g (0.69 mmole) of intermediate 4.3 in 42 ml of THF at 23° C. After stirring for 5 h 30 at 23° C., 137 µl of a 0.5 M solution of $NaHCO_3$ (0.1 eq.) is added. Stirring is maintained for another 5 minutes before filtration of the precipitate formed. The filtrate is concentrated to dryness and the residue is purified using a silica column (dichloromethane/EtOH:95/5 to 90/10). The pure fractions are collected and evaporated in order to produce 171 mg of an orange solid with a yield of 43%. Melting point: 148-150° C.

Example 6

6.1) N-ethyl-10H-phenothiazine-2-carboxamide 5.8 ml (3.3 eq.) of DIEA is added dropwise to a solution of 2.43 g (10 mmoles) of 10H-phenothiazine-2-carboxylic acid, 1.79 g (2.2 eq.) of ethylamine hydrochloride and 4.17 g (1.1 eq.) of HBTU in 50 ml of DMF, cooled down to 0° C. The reaction mixture is stirred for 15 hours at 23° C., and then poured into a mixture of 100 ml of a saturated solution of NaHCO$_3$ and 100 ml of AcOEt. After stirring for a few minutes, the precipitate formed is removed by filtration and the filtrate is decanted. The organic phase is successively washed with water, a 1M solution of citric acid and salt water. The organic solution is dried over sodium sulphate, filtered and concentrated to dryness under vacuum. The solid obtained is suspended in Et$_2$O, triturated and filtered. A beige solid is obtained with a quantitative yield. Melting point: 150-151° C.

6.2) N-ethyl-10H-phenothiazine-2-carbothioamide

The experimental protocol used is the same as that described for intermediate 1.5, with intermediate 6.1 replacing 10H-phenothiazine-2-carboxamide. 2.17 g of a yellow solid is obtained with a yield of 60%. Melting point: 155-156° C.

6.3) Methyl N-ethyl-10H-phenothiazine-2-carbimidothioate hydrochloride

The experimental protocol used is the same as that described for intermediate 1.6 using iodomethane, with intermediate 6.2 replacing intermediate 1.5. The salified compound obtained in the form of the hydroiodide is then divided between a saturated solution of NaHCO$_3$ and AcOEt. After decantation, the organic phase is washed with water and salt water, dried over sodium sulphate and filtered. 1.1 eq. of a 1N titrated solution of HCl in anhydrous Et$_2$O is then added to this organic solution cooled down to 0° C. After stirring for one hour at 23° C., the reaction mixture is concentrated to dryness under vacuum. The evaporation residue is finally suspended in Et$_2$O and filtered. A dark red solid is obtained. Melting point: 142-143° C.

Example 7

N$^1$-[(3S)-2-hydroxytetrahydrofuran-3-yl]-N$^2$-[imino (10H-phenothiazin-2-yl)methyl]-L-leucinamide hydrochloride A solution of 2.5 g (4.4 mmoles) of the compound of Example 5 in 1 liter of distilled water is deposited at the top of a column containing approximately 10 equivalents of a Dowex-1×2 exchange resin previously equilibrated in the chloride form. The compound is eluted dropwise from the column using distilled water. The fractions containing the expected compound are collected and lyophilized. 1.55 g (yield: 74%) of a yellow solid is obtained. Melting point: 202-205° C.

Pharmacological Study of the Compounds of the Invention:

The compositions according to the invention are the following:

Composition 1

N$^1$-[(3S)-2-hydroxytetrahydrofuran-3-yl]-N$^2$-[imino (10H-phenothiazin-2-yl)methyl]-L-leucinamide (Example 5)+α-methylprednisolone hydroiodide Composition 2

(3S)-3-{[N-(10H-phenothiazin-2-ylcarbonyl)-L-leucyl]amino}tetrahydrofuran-2-yl acetate+α-methylprednisolone Composition 3

N$^1$-[(3S)-2-hydroxytetrahydrofuran-3-yl]-N$^2$-[imino (10H-phenothiazin-2-yl)methyl]-L-leucinamide hydrochloride (Example 7)+α-methylprednisolone Protective Effect of the Compounds According to the Invention on Cell Death Induced by Maitotoxin on Human Skeletal Cells (SKM)

The principle of the test is the following: maitotoxin is a toxin which causes the opening of the calcium channels of cells. The resulting intra-cellular flow of calcium is at the origin of the death of the cell. During this process of cell death, a cysteine-dependent protease, calpain, is activated, and an abundance of free radicals is produced. The test consists of incubating the cells in the presence of the composition to be tested, in order to delay or inactivate cell death and thus determine the protective effect.

The myoblasts are seeded at 2500 cells per well in 96-well plates in a DMEM 10% FCS (foetal calf serum) culture medium supplemented with amphotericin B, human recombinant epidermal growth factor and dexamethasone. Three days after seeding, the cells have adhered to the base of the well, the differentiation of the cells to myotubes is induced by adding 100 µl of DMEM F12 medium containing 2% horse serum. After three more days, 100 µl of compound to be tested are placed at the bottom of the well. After incubation for one hour at 37° C. under an atmosphere of 5% CO$_2$, the maitotoxin (MTX) (Wako, ref: 131-10731) is added to evaluate the protective effect (concentration-effect) of the compound to be tested on cell death.

After an incubation time of 24 h, the culture medium is replaced by a DMEM 10% FCS medium supplemented by WST-1. WST-1 (Roche, reference 1644807) is a reagent which stains metabolically active cells, i.e. live cells. The cells are incubated for 1 hour in the presence of WST-1. Then the number of live cells is determined using a Perkin-Elmer Wallac Envision 2101 device by reading the absorbance at 450 nm. The concentration-effect of the products on the cell survival rate is then calculated.

The EC$_{50}$ (concentration of the substance to be tested which protects 50% of the cells from cell death) is calculated from this concentration-effect. The CE$_{50}$ is deduced by linear regression: concentration with respect to the percentage of protection. The mathematical method used is the isobologram approach described in: "Drug synergism and dose-effect data analysis, Ronald J. Tallarida, Chapman & Hall/CRC, 2000".

The results obtained are shown in Table 1 below:

| Compounds | | Proportions | Cell mortality rate induced by the toxin | EC$_{50}$ μM After incubation for 24 h with the toxin |
|---|---|---|---|---|
| Compound of Example 5 | A | 1 | 84% | 6.26 μM |
| α-methylprednisolone | B | 1 | | 87.64 μM |
| Composition 1 | (B + A) | 0.925 B + 0.075 A | | 28.12 μM |
| Theoretical additive effect expected for Composition 1 | (B + A) | 0.925 B + 0.075 A<br>Zadd. = 0.925 × 87.64 μM + 0.075 × 6.26 μM | | 81.53 μM |
| (3S)-3-{[N-(10H-phenothiazin-2-ylcarbonyl)-L-leucyl]amino}tetrahydrofuran-2-yl-acetate | C | 1 | 97% | 29.10 μM |
| α-methylprednisolone | B | 1 | | 106.98 μM |
| Composition 2 | (B + C) | 0.8 B + 0.2 C | | 50.51 μM |
| Theoretical additive effect expected for Composition 2 | (B + C) | 0.8 B + 0.2 C<br>Zadd. = 0.8 × 106.98 μM + 0.2 × 29.10 μM | | 91.40 μM |
| Compound of Example 7 | D | 1 | 96% | 5.92 μM |
| α-methylprednisolone | B | 1 | | 169.27 μM |
| Composition 3 | (B + D) | 0.952 B + 0.048 D | | 52.50 μM |
| Theoretical additive effect expected for Composition 3 | (B + D) | Zadd. =<br>0.952 × 169.27 μM + 0.048 × 5.92 μM | | 161.49 μM |
| Composition 3 | (B + D)' | 0.909 B + 0.091 D | | 38.59 μM |
| Theoretical additive effect expected for Composition 3 | (B + D)' | 0.909 B + 0.091 D<br>Zadd. =<br>0.909 × 169.27 μM + 0.091 × 5.92 μM | | 154.42 μM |
| Composition 3 | (B + D)" | 0.833 B + 0.167 D | | 27.86 μM |
| Theoretical additive effect expected for Composition 3 | (B + D)" | 0.833 B + 0.167 D<br>Zadd. =<br>0.833 × 169.27 μM + 0.167 × 5.92 μM | | 142.05 μM |
| Composition 3 | (B + D)'" | 0.714 B + 0.286 D | | 12.83 μM |
| Theoretical additive effect expected for Composition 3 | (B + D)'" | 0.714 B + 0.286 D<br>Zadd. =<br>0.714 × 169.27 μM + 0.286 × 5.92 μM | | 122.60 μM |

Composition 1 in this test has an EC$_{50}$ of 28.12 μM after incubation for 24 hours in the presence of maitotoxin.

A comparative test is carried out with α-methylprednisolone which is a compound used for the treatment of Duchenne's muscular dystrophy. In comparison, with the same test and under the same conditions, α-methylprednisolone has an EC$_{50}$ of 87.64 μM after incubation for 24 hours in the presence of maitotoxin.

The synergistic effect between the compounds is demonstrated by a calculation. In fact by the isobologram method, it is calculated that a simple addition of the effect of the constituents of Composition 1 would have shown a EC$_{50}$ of 81.53 μM. An EC$_{50}$ of 28.12 μM has been shown, clearly indicating a synergistic effect between the constituents.

Composition 2 in this test has an EC$_{50}$ below 50.51 μM after incubation for 24 hours in the presence of maitotoxin.

A comparative test is carried out with α-methylprednisolone under more drastic conditions (97% induced mortality). In comparison, with the same test and under the same conditions, α-methylprednisolone has an EC$_{50}$ of 106.98 μM after incubation for 24 hours in the presence of maitotoxin.

The synergistic effect between the compounds is demonstrated by a calculation. In fact by the isobologram method, it is calculated that a simple addition of the effect of the constituents of Composition 2 would have shown an EC$_{50}$ of 91.40 μM. EC$_{50}$ of 50.51 μM has been shown, clearly indicating a synergistic effect between the constituents.

Composition 3 has respectively, in this test, EC$_{50}$s of 52.50 μM; 38.59 μM; 27.86 μM and 12.83 μM depending on the various proportions of α-methylprednisolone and compound of Example 7 used (0.952/0.048; 0.909/0.091; 0.833/0.167 and 0.714/0.286, respectively) after incubation for 24 hours in the presence of maitotoxine.

A comparative test is carried out with α-methylprednisolone under the same drastic conditions (96% induced mortality). In comparison, with the same test and under the same conditions, α-methylprednisolone has an EC$_{50}$ of 169.27 μM after incubation for 24 hours in the presence of maitotoxin.

The synergistic effect between the compounds is demonstrated by a calculation. In fact by the isobologram method, it is calculated that a simple addition of the effect of the constituents of Composition 3 would have shown EC$_{50}$s of 161.49 μM; 154.42 μM; 142.05 μM and 122.60 μM depending on the different proportions of α-methylprednisolone/compound of Example 7 used, namely 0.952/0.048; 0.909/0.091; 0.833/0.167 and 0.714/0.286 respectively. EC$_{50}$s of 52.50 μM; 38.59 μM; 27.86 μM and 12.83 μM have been shown respectively, clearly indicating a synergistic effect between the constituents.

The invention claimed is:

1. A composition comprising α-methyl prednisolone, or a salt thereof, and N$^1$-[(3S)-2-hydroxytetrahydrofuran-3-yl]-N$^2$-[imino(10H-phenothiazin-2-yl)methyl]-L-leucinamide, or a salt thereof, wherein the α-methyl prednisolone or a salt thereof and N$^1$-[(3S)-2-hydroxytetrahydrofuran-3-yl]-N$^2$-[imino(10H-phenothiazin-2-yl)methyl]-L-leucinamide or a salt thereof are present in a synergistically effective weight ratio of 1 part α-methyl prednisolone or a salt thereof to at least 0.1 parts N$^1$-[(3S)-2-hydroxytetrahydrofuran-3-yl]-N$^2$-[imino(10H-phenothiazin-2-yl)methyl]-L-leucinamide.

2. A method of treating inflammatory or immunological diseases, cardiovascular diseases, cerebro-vascular diseases, disorders of the central or peripheral nervous system, cachexia, sarcopenia, hearing loss, osteoporosis, muscular dystrophies, cancerous or non-cancerous proliferative diseases, cataract, rejection reactions following organ transplantation, auto-immune diseases, viral diseases or cancer comprising administering the composition of claim 1 to a patient in need thereof.

3. A method of treating muscular distrophies comprising administering the composition of claim 1 to a patient in need thereof.

4. A pharmaceutical composition comprising the composition of claim 1 or a pharmaceutically acceptable salt thereof.

5. A pharmaceutical, veterinary, cosmetic, or food product comprising the composition of claim 1.

6. The method of claim 3, wherein the muscular distrophy is Duchenne's muscular dystrophy, Becker's muscular dystrophy, myotonic muscular dystrophy or Steiner's disease, congenital muscular dystrophy, limb girdle muscular dystrophy or facioscapulohumeral muscular dystrophy comprising administering the composition of claim 1 to a patient in need thereof.

* * * * *

UNITED STATES PATENT AND TRADEMARK OFFICE
CERTIFICATE OF CORRECTION

PATENT NO.        : 8,642,591 B2                                      Page 1 of 1
APPLICATION NO.   : 12/282131
DATED             : February 4, 2014
INVENTOR(S)       : Pignol et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 844 days.

Signed and Sealed this

Twenty-ninth Day of September, 2015

Michelle K. Lee
*Director of the United States Patent and Trademark Office*